United States Patent [19]

Dattagupta

[11] Patent Number: 4,692,509

[45] Date of Patent: Sep. 8, 1987

[54] RADIOACTIVE LABELING OF PROTEINS WITH NUCLEOSIDES OR NUCLEOTIDES

[75] Inventor: Nanibhushan Dattagupta, New Haven, Conn.

[73] Assignee: Molecular Diagnostics, Inc., West Haven, Conn.

[21] Appl. No.: 675,373

[22] Filed: Nov. 27, 1984

[51] Int. Cl.⁴ .................... A61K 43/00; A61N 5/12
[52] U.S. Cl. ............................... 530/303; 422/61; 424/1.1; 435/6; 435/29; 435/34; 530/380; 530/389; 530/395; 530/406; 530/410; 530/411
[58] Field of Search ............ 260/112 R, 112 B; 424/1.1; 435/6, 29, 34; 536/27; 422/61; 530/303, 380, 389, 395, 406, 410, 411

[56] References Cited

U.S. PATENT DOCUMENTS

| | | | |
|---|---|---|---|
| 4,259,232 | 3/1981 | Carrico et al. | 260/112 R |
| 4,358,535 | 11/1982 | Falkow et al. | 435/5 |
| 4,469,796 | 9/1984 | Axen et al. | 435/7 X |

FOREIGN PATENT DOCUMENTS 0097373  1/1984  European Pat. Off. .
2019408  10/1979  United Kingdom .

OTHER PUBLICATIONS

DNA Replication, Kornberg (1980), pp. 4–6.
Biochem. Soc. Trans., 12(2), 1984, 279–280, Woodhead et al.

*Primary Examiner*—Howard E. Schain
*Attorney, Agent, or Firm*—Sprung, Horn, Kramer & Woods

[57] ABSTRACT

A radioactively labeled protein comprising a protein, and a radioactive nucleoside or nucleotide, the protein being covalently linked to the nucleoside or nucleotide. Advantageously the linkage is through an $NH_2$ group of the protein and through a carbonyl group of a ring-opened sugar moiety of the nucleoside or nucleotide. The protein can be insulin, an immunoglobulin or protein A. The radioactive moiety may be a P, C, S, H, I or Hg atom. The labels can be used to indicate the presence and amount of the protein in a biological assay.

12 Claims, No Drawings

RADIOACTIVE LABELING OF PROTEINS WITH NUCLEOSIDES OR NUCLEOTIDES

This application relates to the radioactive labeling of proteins.

Radioactive labeling of proteins is essential for the estimation of small quantities of the material. The state-of-the-art method involves radioactive iodination but it usually modifies the aromatic residues of the protein. The use of Bolton-Hunter reagent causes the modification of nonaromatic residues but the half-life of the reagent and its solubility in water, create unique problems in handling.

It is accordingly an object of the present invention to provide a way of radioactively labeling proteins easily, with minimum modification of the protein structure and without the noted disadvantages.

These and other objects and advantages are realized in accordance with the present invention pursuant to which the protein is covalently linked to a nucleoside or nucleoside phosphate (i.e., nucleotide) which carries the radioactivity. The covalent link is produced by splitting a sugar ring of the nucleoside to form an aldehyde group which will form a Schiff's base upon reaction with an amino group of the protein, optionally followed by reduction to convert the —N=CH— to the more stable —NH—CH$_2$—. The radioactivity can be anywhere on the nucleoside or nucleotide moiety as in a P, H, C, S, I, Hg, or other atom.

In this way it is not necessary to use costly $^{125}$I and the half-life can be selected by the choice of the radioactive site.

It is even possible to use radioactive iodine labeling as by using an iodine-labeled base in the nucleoside and the process of labeling will avoid the complications of the solubility of Bolton-Hunter reagent or the involvement of several complex systems or different kinds of reagents which are difficult to handle.

The protein so labeled can be used in conventional immunoassays since the radioactive moiety is attached to a few or even only a single site on the protein, leaving the balance of the protein free for interaction.

The protein to be labeled can be any protein having a free NH$_2$ radical or a radical convertable thereto. Enzymes, antibodies, antigens and the like are all suitable, e.g., insulin, protein A, papain, immunoglobulins such as IgG, horseradish peroxidase, β-galactosidase, and the like.

The nucleoside or nucleoside phosphate (nucleotide) advantageously carries its radioactive label before reaction with the protein. In one simple form, radioactive phosphorus can be present in a nucleoside mono-, di-, or tri-phosphate. Because of the short half-life of $^{32}$P, phosphate can result in relatively high levels of radioactivity remote from the protein whereas corresponding levels of radioactivity by direct reaction of the protein with radioactive iodine would have required much iodine and would have modified the protein considerably.

The nucleoside or nucleotide can be radioactively labeled on a carbon, hydrogen or other atom, many of which are commercially available. A sugar ring of the nucleoside or nucleotide can be opened by periodate oxidation in known manner, as described more fully in application Ser. No. 582,503, filed Feb. 22, 1984, now pending, the disclosure of which is incorporated herein by reference. This produces a carbonyl moiety needed for linkage to the protein.

Then the carbonyl-containing radioactive nucleoside or nucleotide is reacted with the —NH$_2$— containing protein, again in manner known for producing Schiff's bases. Advantageously the protein is present in stoichiometric amount or in excess, calculations being based on the number of —NH$_2$ groups of the protein molecule sought to be labeled.

When greater stability is desired, the Schiff's base linkage can be stabilized by saturation, i.e., by reduction with a selective hydrogenating agent such as sodium borohydride.

In an alternate embodiment of the present invention, the covalent link between the protein and nucleoside can be through a sulfur atom, employing a suitable sulfur-containing nucleoside such as one carrying an —SH moiety. This can be linked to a protein also carrying an —SH moiety forming an —S—S— linkage in known manner, as described in application Ser. No. 612,983, filed May 23, 1984, now pending, and application Ser. No. 612,983, filed May 23, 1984, now pending, the disclosures of which are incorporated herein by reference.

The invention will be further described in the following illustrative examples where all parts are by weight unless otherwise expressed or apparent. These examples demonstrate that this new method of labeling does not affect the protein's structure function relationship. Several enzymes have been labeled and no significant alteration of enzyme activity could be detected after labeling the molecules with oxidized radioactive nucleoside phosphate.

EXAMPLE I

Labeling of horseradish peroxidase (HRP)

The labeling has been done in three steps: oxidation of nucleoside triphosphate, reaction of the oxidized product with the enzyme (HRP) and the reduction of the Schiff's base.

(1) Oxidation of $^{14}$C labeled ATP:

5 μl of 1 mg/ml sodium metaperiodate in 100 mM sodium acetate, pH 5 buffer is added to 500 μl $^{14}$C labeled ATP, 0.1 mg/ml, ∼5 μci (New England Nuclear). Oxidation is effected at room temperature for 30 minutes. (The oxidation reaction can be carried out between 0°–80° C.) The oxidized product does not have to be purified when the coupling reaction is done with a protein lacking glycosidic residues. Otherwise the oxidation is carried out by mixing in more than 1:1 molar ratio of the nucleoside to metaperiodate. The reaction is quantitative when pure compounds are used.

(2) Coupling with protein:

The oxidized nucleoside phosphate (in 505 μl) is adjusted to pH 8 by adding 5 μl 1 mM aqueous sodium hydroxide solution. To this 510 μl solution 500 μl horseradish peroxidase solution (1 mg/ml in 0.1M sodium bicarbonate buffer, pH 8) is added and the couping reaction is carried by incubation of this mixture at room temperature for an hour.

(3) Reduction of the Schiff's base:

1.01 ml solution from step (2) containing the Schiff's base is reduced by adding 200 mM 125 μl aqueous sodium borohydride solution and incubating the mixture at room temperature for two hours.

In a duplicate experiment 125 μl borohydride solution has been added in 5×25 μl aliquots with 30 minute intervals between each addition.

After the final step, the enzyme solution is dialyzed against distilled water. A control experiment is run with an enzyme solution without nucleoside triphosphate.

(4) Test of enzyme activity of the labeled enzyme:

After the coupling reaction, the enzyme is dialyzed against water and assayed in a known manner as follows:

50 µl 1% o-dianisidine in methyl alcohol is added to 6 ml freshly prepared 0.003% hydrogen peroxide in 10 mM phosphate buffer, pH 6.0 and 2.9 ml of the mixture is taken in a cuvette. The rest of the mixture is added to a reference cuvette. Then 0.1 ml of the enzyme solution is added and absorbance is monitored at 460 nm in a Varian 2200 spectophotometer. The control enzyme solution is also assayed in a similar fashion. The plots of absorbance at 460 nm against time are substantially identical.

EXAMPLE II

Immunoassay for anti DNA-antibody for the diagnosis of Systemic Lupus Erythematosus (SLE)

The commerically available anti-immunoglobulin antibody has been labeled with $^{14}C$ labeled oxidized ATP as in Example I. After the labeling, the labeled and the control samples are dialyzed against PBS buffer. Double stranded DNA (native) is covalently fixed to a cellulose via a photachemical reaction with immobilized aminomethyl triozsalen made by the process described in application Ser. No. 511,064, filed July 5, 1983, now pending, the disclosure of which is incorporated herein by reference. About 100 µl of this support with adsorbed DNA is taken in a test tube and 100 µl mg/ml bovine serum albumin (BSA) in PBS is added. The suspension is then divided into 5 test tubes and centrifuged to remove unadsorbed BSA solution. The support is washed gently with PBS, then incubated with 100 µl of an appropriate serum dilution from a SLE patient. The mixture is gently shaken for 60 minutes and then washed 5 times with PBS buffer. Then radioactively labeled anti-immunoglobulin antibody is added, incubated for 60 minutes, then washed 5 times with PBS. The mixture is then irradiated at 260 nm light in the presence of 1% SDS for 30 minutes to release bound DNA in solution, and the radioactivity of the mixture is counted after adding scintillation fluid.

Any radioactivity associated with the beads before photodecomposition or in solution after the photodissociation is an indication of the presence of anti-double stranded DNA antibody in the patient's serum and hence the presence of the disease.

In other runs, employing 32P and $^{125}I$ labeled nucleotides, radioactivity can be measured without the need for photoreversal, i.e., irradiation at 260 nm.

It will be understood that the specification and examples are illustrative but not limitative of the present invention and that other embodiments within the spirit and scope of the invention will suggest themselves to those skilled in the art.

What is claimed:

1. A radioactively labeled protein comprising a protein, and a radioactive nucleoside or nucleotide, wherein a radioactive moiety is present in the nucleoside or nucleotide, the protein being convalently linked to the nucleoside or nucleotide.

2. A radioactively labeled protein according to claim 1, wherein linkage is through an $NH_2$ group of the protein.

3. A radioactively labeled protein according to claim 2, wherein the linkage is through a carbonyl group of a ring-opened sugar moiety of the nucloeside or nucleotide.

4. A radioactively labeled protein according to claim 1, wherein the radioactive nucleoside or nucleotide carries a radioactive phosphorus atom.

5. A radioactively labeled protein according to claim 1, wherein the radioactive nucleoside or nucleotide carries a radioactive carbon atom.

6. A radioactively labeled protein according to to claim 1, wherein the radioactive nucleoside or nucleotide carries a radioactive iodine hydrogen, sulfur or atom.

7. A radioactively labeled protein according to claim 1, wherein the radioactive nucleoside or nucleotide carries a radioactive mercury atom.

8. A radioactively labeled protein according to claim 1, wherein the protein comprises insulin.

9. A radioactively labeled protein according to claim 1, wherein the protein comprises an immunoglobulin.

10. A radioactively labeled protein according to claim 1, wherein the protein comprises protein A.

11. A radioactively labeled protein according to claim 1, wherein the nucleotide is ATP.

12. A radioactively labeled protein according to claim 1, wherein the protein is linked to a nucleoside.

* * * * *